United States Patent [19]

Cartwright et al.

[11] 4,384,135
[45] May 17, 1983

[54] PREPARATION OF FLUORINE-CONTAINING DIPHENYL ETHERS

[75] Inventors: David Cartwright, Reading; Roger Salmon, Bracknell; Alfred G. Williams, Binfield, all of England

[73] Assignee: Imperial Chemical Industries Limited, London, England

[21] Appl. No.: 226,023

[22] Filed: Jan. 19, 1981

[30] Foreign Application Priority Data

Feb. 5, 1980 [GB] United Kingdom ............... 8003886

[51] Int. Cl.$^3$ ................... C07C 65/21; C07C 25/13; C07C 121/75; C07C 143/74
[52] U.S. Cl. ................... 562/435; 260/465 D; 260/465 F; 560/21; 560/65; 562/465; 564/99; 564/166; 564/171; 568/315; 568/639; 570/127
[58] Field of Search ............... 260/465 F, 465 D; 570/127; 568/639, 315; 564/166, 171, 99; 560/21, 65; 562/435, 465

[56] References Cited

U.S. PATENT DOCUMENTS

| | | | |
|---|---|---|---|
| 3,290,353 | 12/1966 | Battershell et al. | 260/465 G |
| 3,928,416 | 12/1975 | Bayer et al. | 260/465 F X |
| 3,954,829 | 5/1976 | Rohe et al. | 260/465 F |
| 3,957,852 | 5/1976 | Fuyikawa et al. | 260/465 F X |
| 3,966,453 | 6/1976 | Takahashi et al. | 71/105 |
| 3,979,437 | 9/1976 | Theissen | 260/465 D X |
| 4,031,131 | 6/1977 | Johnson | 560/65 |
| 4,285,723 | 8/1981 | Cartwright et al. | 71/103 |

FOREIGN PATENT DOCUMENTS 1668331 3/1971 Fed. Rep. of Germany .
2333848 7/1973 Fed. Rep. of Germany .

OTHER PUBLICATIONS

H. S. Gutowsky et al., Chemisches Zentralblatt, 1953, 124, No. 41, p. 6644.
G. C. Finger et al., Chem. Abs. 1946, 40, No. 13, abs. Running from col. 3733-9 to col. 3734-1.
Methoden der Organischen Chemie (Houben-Weyl) Band VI/3, p. 87.
Methoden der Organischen Chemie (Houben-Weyl) 1962, Band V/3, pp. 162-163.
Chemistry of Organic Fluorine Compounds, by Milos Hudlicky, 1976, pp. 120-121.

Primary Examiner—Dolph H. Torrence
Attorney, Agent, or Firm—Cushman, Darby & Cushman

[57] ABSTRACT

A method of preparing a diphenyl ether compound of the formula (II)

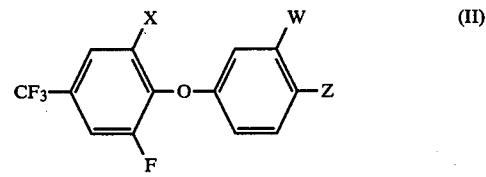

wherein X is F, Cl or Br; Z is hydrogen, halogen, $NO_2$ of CN; and W is methyl, cyano, $CH_3CO$—, or a group —C—OR, wherein R is —OH; —OM wherein M is a cation; $OR^1$ wherein $R^1$ is an optionally substituted aliphatic radical; —$NR^2R^3$ wherein $R^2$ and $R^3$ are each hydrogen or an optionally substituted aliphatic radical; or —$NHSO_2R^4$ wherein $R^4$ is alkyl of 1 to 6 carbon atoms, which comprises reacting a 3-X-substituted-4,5-difluorobenzotrifluoride with a salt of a 3,4-W,Z-substituted phenol. The invention further comprises novel 3-X-4,5-difluorobenzotrifluorides for use in the process.

7 Claims, No Drawings

PREPARATION OF FLUORINE-CONTAINING DIPHENYL ETHERS

This invention relates to chemical processes and intermediates therefor, and in particular to a process of preparing fluorine-containing diphenyl ether derivatives useful as herbicides.

In our European patent application having the publication number 3416 we have disclosed diphenyl ether compounds of the formula (I)

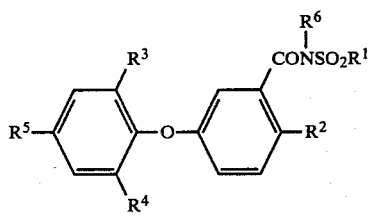

wherein $R^1$ is an alkyl group optionally substituted by one or more fluorine atoms or by an optionally substituted phenyl group; $R^2$ is a hydrogen atom, a fluorine, chlorine, bromine, or iodine atom; or a nitro group; $R^3$ is a hydrogen atom, a fluorine, chlorine, bromine, or iodine atom, an alkyl group, a trifluoromethyl group, or a cyano group; $R^4$ is a hydrogen atom, a fluorine, chlorine, bromine, or iodine atom, or a trifluoromethyl group; $R^5$ is a fluorine, chlorine, bromine, or iodine atom or a trifluoromethyl group; and $R^6$ is a hydrogen atom or an alkyl group of 1 to 4 carbon atoms. These compounds are useful as herbicides. The preparation of compounds of formula (I) wherein one of the groups $R^3$ and $R^4$ is a fluorine atom and the other is a halogen atom and $R^5$ is $CF_3$ by conventional methods may require an inconveniently large number of synthetic stages. Thus, for example, the preparation of the compound (I) in which $R^1$ is methyl, $R^2$ is nitro, $R^3$ is chlorine, $R^4$ is fluorine, $R^5$ is trifluoromethyl, and $R^6$ is hydrogen has been carried out from 4-chloro-3-nitro-benzotrifluoride by the following sequence of reactions:

(1) Reaction of 4-chloro-3-nitrobenzotrifluoride with sodium methoxide to give 4-methoxy-3-nitro-benzotrifluoride (2) Reduction of 4-methoxy-3-nitrobenzotrifluoride to 3-amino-4-methoxybenzotrifluoride (3) Conversion of 3-amino-4-methoxybenzotrifluoride to its diazonium fluoroborate salt and thermal decomposition of the latter to give 3-fluoro-4-methoxybenzotrifluoride (4) Conversion of 3-fluoro-4-methoxybenzotrifluoride to 3-fluoro-4-hydroxybenzotrifluoride by treatment with pyridine hydrochloride.

(5) Nitration of 3-fluoro-4-hydroxy-5-nitrobenzotrifluoride to give 3-fluoro-4-hydroxy-5-nitrobenzotrifluoride.

(6) Reduction of 3-fluoro-4-hydroxy-5-nitro-benzotrifluoride to 3-amino-5-fluoro-4-hydroxy-brenzotrifluoride.

(7) Reaction of 3-amino-5-fluoro-4-hydroxy-benzotrifluoride with 3-methoxycarbonyl-4-nitrofluorobenzene in presence of base to give 3-fluoro-2(3-methoxycarbonyl-4-nitrophenoxy)-4-trifluoromethyl aniline.

(8) Conversion of 3-fluoro-2(3-methoxycarbonyl-4-nitrophenoxy)-5-trifluoromethyl aniline to its diazonium fluoroborate salt and treatment of the latter with cuprous chloride to give methyl 5(2-chloro-6-fluoro-4-trifluoromethylphenoxy)-2-nitrobenzoate.

(9) Hydrolysis of methyl 5(2-chloro-6-fluoro-4-trifluoromethylphenoxy)-2-nitrobenzoate to 5(2-chloro-6-fluoro-4-trifluoromethylphenoxy)-2-nitrobenzoic acid.

(10) Conversion of 5(2-chloro-6-fluoro-4-trifluoromethylphenoxy)-2-nitrobenzoic acid to 5-(2-chloro-6-fluoro-4-trifluoromethylphenoxy)-2-nitro-benzoyl chloride.

(11) Reaction of 5-(2-chloro-6-fluoro-4-trifluoromethylphenoxy)-2-nitro benzoyl chloride with methanesulphonamide to give the required compound, i.e. N-methanesulphonyl-5-(2-chloro-6-fluoro-4-trifluoromethylphenoxy)-2-nitro-benzamide.

The present invention provides an alternative process for preparing compounds of formula (I) wherein one of the groups $R^3$ and $R^4$ is a fluorine atom and the other is a halogen atom. The process may be used to prepare compounds of formula (I) directly, or may be used to prepare intermediate compounds which may themselves be converted into compounds of formula (I) by further steps.

According to the present invention there is provided a process for preparing compounds of the formula (II)

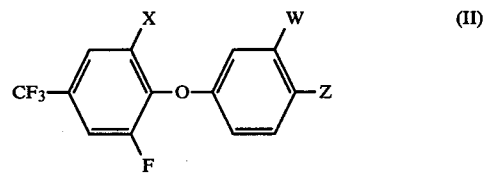

wherein X is fluorine, chlorine, bromine or iodine, Z is hydrogen, fluorine, chlorine, bromine, iodine, nitro, or cyano, and W is a methyl group, a cyano group, an acetyl group, or a group

wherein R is OH; OM wherein M is a cation; $OR^1$ wherein $R^1$ is an optionally substituted aliphatic radical; $-NR^2R^3$ wherein $R^2$ and $R^3$ are each hydrogen or an optionally substituted aliphatic radical; or $-NHSO_2R^4$ wherein $R^4$ is an alkyl radical of 1 to 6 carbon atoms, which comprises reacting a benzotrifluoride derivative of formula (III) with a salt of a phenol derivative (IV) in a solvent or diluent for the reactants, and when W is $-COOH$ or $-CONHSO_2R^4$, acidifying the product of the reaction and recovering the compound of formula (II). The cation M referred to above may be for example a metal cation, for example an alkali metal or alkaline earth metal cation, for example sodium, potassium, magnesium, or calcium. The optionally substituted aliphatic radicals $R^1$, $R^2$ and $R^3$ may each be for example an alkyl radical of 1 to 6 carbon atoms or an alkenyl radical of 3 to 6 carbon atoms, either being optionally substituted by, for example, an alkoxy group of 1 to 4 carbon atoms. The acid used to acidify the reaction product may be, for example, hydrochloric, sulphuric, or phosphoric acid.

The reaction is outlined in Scheme A below:

Scheme A:

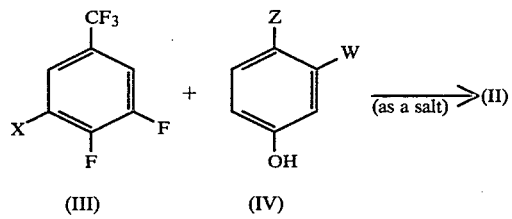

The salt of the phenol derivative (IV) may be for example a salt formed from an inorganic base. Typical inorganic bases include sodium hydroxide, potassium hydroxide, sodium carbonate, and potassium carbonate. When the group W is a carboxyl or —CONHSO$_2$R$^4$ group, two equivalents of the base are used so as to prepare a di-salt. The salt (IV) may if desired be prepared in a solvent different from that used in the subsequent reaction with the benzotrifluoride derivative. For example, the salt may be prepared in methanol. However, when a protic solvent such as methanol is used for the preparation of the salt, it is necessary to remove this solvent before the reaction with the benzotrifluoride is carried out, since the protic solvent could interfere with the reaction desired. The salt of the phenol derivative (IV) need not be separately prepared before carrying out the process of the invention. If preferred, the phenol derivative (IV) and the benzotrifluoride may be reacted in the presence of a base for example an alkali metal carbonate (e.g. anhydrous potassium carbonate), whereby the phenol derivative reacts with the benzotrifluoride as it becomes progressively converted into its salt form by contact with the base. The reaction of the salt (IV) with the benzotrifluoride (III) is preferably carried out in a polar aprotic solvent. Examples of such solvents include dimethylsulphoxide, dimethylformamide, tetramethylenesulphone, N-methylpyrrolidinone and hexamethylphosphoric triamide, and dimethyl acetamide.

Generally the salt (IV) and the benzotrifluoride (III) are used in equimolar amounts; if desired a slight excess of the salt (IV) may be used. The reaction may be conveniently carried out at a temperature from about ambient temperature to 180° C. Reaction times vary, but usually at least two hours is required for significant conversion to take place, and up to 100 hours or more may sometimes be required for substantial completion of reaction.

When sufficient reaction has taken place, the product may be isolated by conventional methods. Where the group W in the starting material (IV) is a carboxyl or a —CONHSO$_2$R$^4$ group, the reaction product will be a salt of a compound of the formula (II). The free acid may be isolated by conventional methods. Thus for example the reaction mixture may be poured into water and the mixture extracted with organic solvent immiscible with water, such as chloroform, ether, dichloromethane or toluene, to remove unchanged benzotrifluoride (III). The mixture may then be acidified to precipitate the free acid. This may then be collected by filtration or may be isolated by extraction with a water-immiscible organic solvent. As noted above, the process of Scheme A may be used to prepare compounds of formula (I) directly; in this case the substituent W in the phenol IV will be a —CONHSO$_2$R$^4$ group. Alternatively, the process of Scheme A may be used to prepare an intermediate which may then be converted into a compound of formula (I) by further steps. Thus, when the group W in the phenol (IV) is a carboxyl group, the product of the process of Scheme A will be a carboxylic acid of the formula (II, W=CO$_2$H). This may be converted into a compound of formula (I) by conversion to the corresponding acid chloride (II, W=COCl) and reaction of the latter with an alkanesulphonamide R$^4$SO$_2$NH$_2$ to give the required compound (I), as described in our European published patent application 3416. Reaction of the acid chloride with alcohols or amines leads to the corresponding esters and amides. When the group W is one of the other substituents listed above, it may be converted to a carboxyl group by known chemical procedures and the compound (II, W=CO$_2$H) so obtained may then be converted to the required compound (I) as described above. Thus, when the group W is a —COOR$^1$ group, that is to say an ester, it may be converted to a carboxyl group by known methods, for example by mild alkaline hydrolysis or by acid hydrolysis. When the group W is a cyano group, it may be converted to a carboxyl group by acid hydrolysis according to known procedures. When the group W is a —CONR$^2$R$^3$ group, it may similarly be converted to a carboxyl group by acid hydrolysis. When the group W is a methyl group, it may be converted to a carboxyl group by oxidation, for example oxidation by alkaline potassium permanganate, or by catalytic oxidation. When the group W is an acetyl group (CH$_3$CO—) it may be converted to a carboxyl group by treatment with a halogen (chlorine, bromine, or iodine) in presence of alkali (the haloform reaction). It will be apparent to those skilled in the art that when the substituent Z required in the final products (I) is other than hydrogen, it may be possible to introduce it either during or after the process step of Scheme A. Thus, when Z is required to be a nitro group, the process of Scheme A could be carried out using a phenol derivative (IV) in which Z was a nitro group. Alternatively, the process of Scheme A could be carried out with a phenol derivative (IV) in which Z was hydrogen. The required nitro group could then be introduced into the compound (II) in which Z was hydrogen, by treating the latter with a nitrating agent. Examples of nitrating agents include nitric acid/sulphuric acid, potassium nitrate/sulphuric acid, and nitric acid/sulphuric acid/acetic anhydride. A co-solvent may be used if desired. Examples of co-solvents include dichloromethane, ethylene dichloride, chloroform, and tetrachloroethylene.

The process of Scheme A may also be carried out using an alkali metal fluoride instead of a conventional base such as potassium hydroxide. Examples of alkali metal fluorides include sodium fluoride, potassium fluoride, and caesium fluoride. As another alternative to the use of a conventional base, a phase transfer catalyst may be used. A still further alternative comprises the use of a crown ether.

The benzotrifluoride derivatives (III) required for use in Scheme A are believed to be novel compounds and form part of the present invention. They may be prepared for example by reacting a 3,4,5-trihalogenobenzotrifluoride of the formula

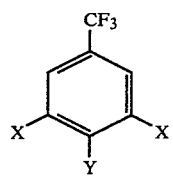

wherein X is fluorine, chlorine, bromine or iodine, and Y is fluorine or chlorine provided that X and Y are not both fluorine, with an alkali metal fluoride. The desired 3-halogeno-4,5-difluorobenzotrifluoride may be recovered by distillation. Compounds of formula (III) wherein X is fluorine or chlorine and Y is fluorine may be prepared for example, by heating 3,4,5-trichlorobenzotrifluoride with an alkali metal fluoride, optionally in the presence of a polar aprotic solvent. The alkali metal fluoride may be, for example, caesium or potassium fluoride.

Examples of polar aprotic solvents include dimethyl sulphoxide, dimethylformamide, tetramethylenesulphone, N-methyl pyrrolidinone, and hexamethylphosphoric triamide. Alternatively, liquid hydrogen fluoride can be used as a solvent. Temperatures for the reaction may range from 130° to 200° C.; or may be lower if liquid hydrogen fluoride is the solvent. A catalyst may be used to accelerate the reaction; examples of catalyst include crown ethers and phase transfer catalysts. The product of the reaction may be isolated by conventional methods, for example by fractional distillation. Usually the reaction of 3,4,5-trichlorobenzotrifluoride with an alkali metal fluoride produces a mixture of 3,4,5-trifluorobenzotrifluoride and 3-chloro-4,5-difluoro-benzotrifluoride. The proportions can be varied by altering the length of time for which the reaction is carried on, and by altering the reaction temperature. Using caesium fluoride in sulpholane as solvent at a temperature of 180° C. for 4.5 hours for example gives a mixture containing about 5 parts of, 3-chloro-4,5-difluoro-benzotrifluoride to 1 part of 3,4,5-trifluorobenzotrifluoride. The 3-chloro-4,5-difluorobenzotrifluoride can be separated and re-heated with more alkali metal fluoride to convert it into 3,4,5-trifluorobenzotrifluoride.

Since, as noted above, an alkali metal fluoride can be used as the base in the process of Scheme A, there is the possibility of converting 3,4,5-trichlorobenzotrifluoride and related 3,4,5-trihalogenobenzotrifluorides to diphenyl ethers in a "one pot" reaction. Thus, for example, the 3,4,5-trichlorobenzotrifluoride would be heated in sulpholane with caesium or potassium fluoride to convert it to 3-chloro-4,5-difluorobenzofluoride. An appropriate 3,4-W,Z-substituted phenol would then be added, with additional potassium or caesium fluoride if necessary, and the mixture heated to form the required diphenyl ether.

3,4,5-Trihalogenobenzotrifluoride required for the preparation of the fluorinated benzotrifluorides (III) may be prepared for example by the process outlined in Scheme B below: (In Scheme B, Y stands for chlorine, bromine or fluorine).

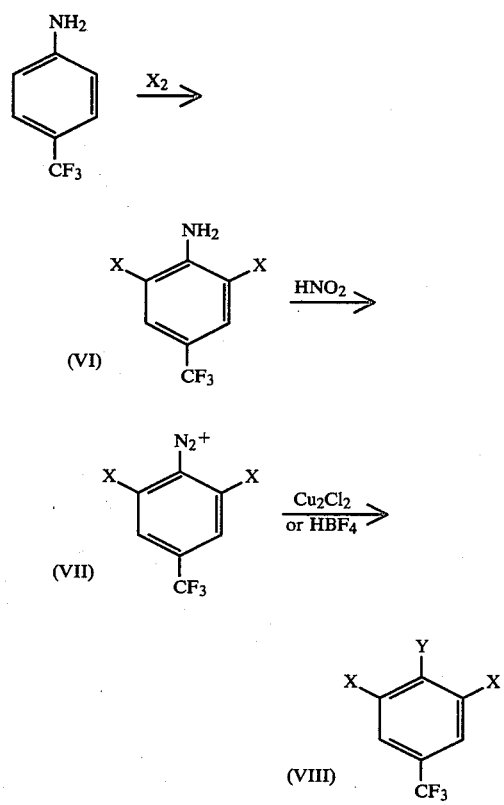

Scheme B

In Scheme B, 4-aminobenzotrifluoride is treated with a halogenating agent $X_2$, which may for example be elemental chlorine, bromine, or iodine, or may be a compound containing an active halogen, for example sulphuryl chloride, N-chloro-succinimide, or N-bromosuccinimide. The halogeno compound (VI) so obtained may then be converted to a 3,4,5-trihalogenobenzotrifluoride by diazotisation with nitrous acid to give the diazonium salt (VII). This is then treated with cuprous chloride to give the corresponding chloro compound (VIII, Y=Cl) or with fluoboric acid followed by heating or photolysis of the isolated diazonium fluoborate salt (Balz-Schiemann reaction) to give the corresponding fluoro compound (VIII, Y=F). It will be seen that Scheme B may be used not only to prepare 3,4,5-trichlorobenzotrifluoride, but also other 3,4,5-trihalogenobenzotrifluorides, for example 3,5-dichloro-4-fluorobenzotrifluoride, 3,5-dibromo-4-fluorobenzotrifluoride, and 3,5-dibromo-4-chlorobenzotrifluoride. These may be reacted with an alkali metal fluoride as described above for 3,4,5-trichlorobenzotrifluoride, in order to obtain the starting materials (III) required for Scheme A.

In an alternative method for preparing the 3,4,5-trihalogenobenzotrifluorides (VIII) the process of Scheme C may be used.

Scheme C

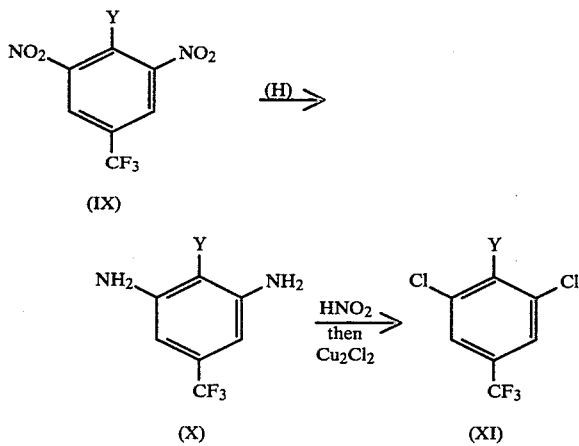

In Scheme C, Y stands for fluorine, chlorine, or bromine. According to Scheme C, a 4-halogeno-3,5-dinitrobenzotrifluoride (IX) is reduced by conventional procedures to a 4-halogeno-3,5-diaminobenzotrifluoride (X). This is then converted by conventional procedure to a bis-diazonium salt which is in turn treated with cuprous chloride by a well-known procedure to give the 4-halogeno-3,5-dichlorobenzotrifluoride (XI).

Variations of Scheme C are possible. Thus, the diamino compound (X) could be treated with nitrous acid to form the bis-diazonium salt. This could then be treated with hydrofluoric acid and heated to give the 2,6-difluoro compound corresponding to the 2,6-dichloro compound (XI). Another variation comprises treating the dinitro compound (IX) with chlorine to displace the nitro groups and form the dichloro compound (XI) directly. Yet a further variation comprises treating compound (IX) with an alkali metal fluoride or with liquid hydrogen fluoride to form 3,4,5-trifluorobenzotrifluoride.

Compounds of formula (III) above may also be used to prepare diphenyl ethers other than those of formula (II) above. Thus for example they may be used to prepare diphenyl ethers of formula (XIII), as shown in Scheme E below:

Scheme E

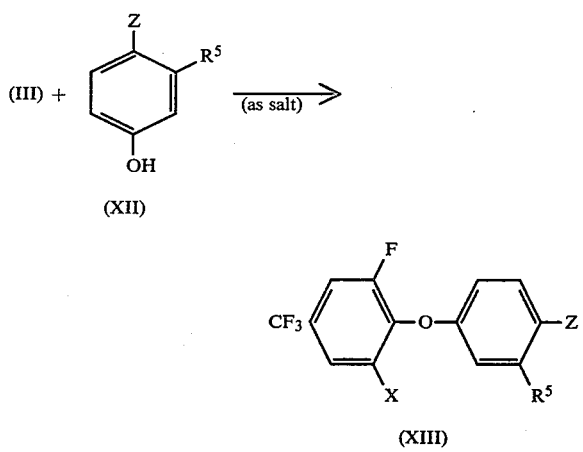

In Scheme E, the symbol $R^5$ may stand for hydrogen, a group $-OR^6$ in which $R^6$ is an optionally substituted aliphatic radical, for example an optionally substituted (e.g. halogeno) alkyl radical of 1 to 6 carbon atoms; halogen (i.e. fluorine, chlorine, bromine, or iodine); a group

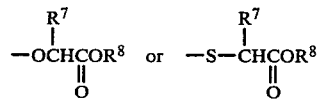

wherein $R^7$ is alkyl of 1 to 4 carbon atoms and $R^8$ is hydrogen or an optionally substituted aliphatic radical for example an alkyl radical of 1 to 6 carbon atoms; an amino group $-NR^9R^{10}$ wherein $R^9$ is hydrogen, an optionally substituted aliphatic radical (e.g. an alkyl radical of 1 to 6 carbon atoms) or an alkylcarbonyl radical of 2 to 6 carbon atoms, and $R^{10}$ is hydrogen or an optionally substituted aliphatic radical (e.g. alkyl of 1 to 6 carbon atoms); or an optionally substituted alkyl radical (e.g. an alkyl radical of 1 to 6 carbon atoms).

The symbol X and Z in Scheme E have the meanings previously assigned to them, but Z may also be a group

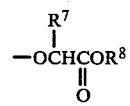

as defined above.

The reaction outlined in Scheme E may be carried out and the product isolated under the conditions described for Scheme A above. When the substituent Z in the final product is other than hydrogen, it may be introduced either as a substituent in the phenol (XII) or alternatively it may be introduced into the product (XIII) of Scheme E.

Thus when Z is to be nitro, it is possible either to carry out the process of Scheme E with a phenol (XII) in which Z is nitro, or to use a phenol (XII) in which Z is hydrogen and then to nitrate the diphenyl ether (XIII) in which Z is hydrogen.

By way of illustration of the usefulness of the benzotrifluoride compounds of the invention as intermediates, the following compounds having herbicidal properties were prepared from 3-chloro-4,5-difluorobenzotrifluoride and 3,4,5-trifluorobenzotrifluoride (referred to below as CDFB and TFB respectively). Except where otherwise stated, the reaction was carried out in the presence of a base (usually potassium carbonate) and in a solvent (usually dimethyl sulphoxide or 2-butanone):

4-(2-Chloro-6-fluoro-4-trifluoromethylphenoxy)benzonitrile (m.p. 77°–78°) from 4-cyanophenol and CDFB;

4-(2,6-Difluoro-4-trifluoromethylphenoxy)benzonitrile (m.p. 76°–77°) from 4-cyanophenol and TFB;

Propyl 2[4(2-chloro-6-fluoro-4-trifluoromethylphenoxy)]-propionate (oil) from propyl 2(4-hydroxyphenoxy)propionate and CDFB;

Propyl 2[4(2,6-difluoro-4-trifluoromethylphenoxy)-phenoxy]-propionate, from propyl 2(4-hydroxyphenoxy)propionate and TFB;

3-Chloro-4-(3-ethoxyphenoxy)-5-fluorobenzotrifluoride (oil) from 3-ethoxyphenol and CDFB;

3-Chloro-4-(2,4-dinitro-5-ethoxyphenoxy)-5-fluorobenzotrifluoride (m.p. 119°–120°) from nitration of the last foregoing compound with potassium nitrate in the presence of concentrated sulphuric acid.

4-(2-Chloro-6-fluoro-4-trifluoromethylphenoxy)nitrobenzene (m.p. 78°–79°) from p-nitrophenol and CDFB;

4-(2-Chloro-6-fluoro-4-trifluoromethylphenoxy)-2-hydroxynitrobenzene (oil) from 2,4-dihydroxy nitrobenzene and CDFB;

Ethyl 2[5(2-Chloro-6-fluoro-4-trifluoromethylphenoxy) 2-nitrophenoxy]propionate (oil), from the last foregoing compound and ethyl 2-bromopropionate.

3-Chloro-4-(3-ethoxy-4-nitrophenoxy)-5-fluoro-benzotrifluoride (m.p. 90°–91°) made by nitration of 3-chloro-4-(3-ethoxyphenoxy)-5-fluorobenzotrifluoride with sodium nitrite and trifluoroacetic acid.

The invention is illustrated by the following Example, in which all parts are by weight and all temperatures in degrees Celsius unless otherwise stated.

EXAMPLE 1

This Example illustrates the preparation of N-methanesulphonyl-5(2-chloro-6-fluoro-4-trifluoromethylphenoxy)-2-nitrobenzamide by the process of claim 1.

N-Methanesulphonyl-5-hydroxy-2-nitrobenzamide (1.04 g) and 3-chloro-4,5-difluorobenzotrifluoride (0.9 g) were stirred with anhydrous potassium carbonate (0.6 g) in dimethylsulphoxide (20 ml) at 110° C. for 24 hours and then left overnight at room temperature. The mixture was then poured into dilute hydrochloric acid (150 ml) and the solid filtered off and crystallised from ethanol/water. The solid was then dissolved in ether and repeatedly washed with brine until the bright yellow colour had almost gone. The extract was then dried and evaporated to give the required compound (1.1 g), identified by comparison of its melting point 171°–172° C.) and infra-red spectrum with that of an authentic sample of the compound prepared by the alternative eleven-stage route described above.

The N-methanesulphonyl-5-hydroxy-2-nitrobenzamide used in the above reaction was prepared as follows:

(a) Preparation of 3-ethoxycarbonyloxybenzoic acid.

3-Hydroxybenzoic acid (13.8 g) was dissolved in a solution of sodium hydroxide (8 g) in water (50 ml) and stirred at 0°–5° with cooling while ethyl chloroformate was added dropwise. When addition was complete the solution was warmed to room temperature and stirred for 2 hours. The solution was acidified with 2 molar sulphuric acid. The white solid which separated was washed with water. The solid was taken up in chloroform and the solution dried (MgSO$_4$) and evaporated to give 3-ethoxycarbonyloxybenzoic acid (14 g) with a melting point of 70°–72°.

(b) Preparation of 5-ethoxycarbonyloxy-2-nitrobenzoic acid.

Finely ground 3-ethoxycarbonyloxybenzoic acid (10.5 g) was added with stirring to concentrated sulphuric acid at 2°. A mixture of concentrated sulphuric acid (10 ml) and 70% nitric acid (4.5 g) was then added dropwise with stirring, keeping the temperature at 5° or below. When addition was complete, the solution was stirred for another 30 minutes and then poured into ice and water (200 ml). The white solid which separated was washed with water and taken up in chloroform. The solution was dried (MgSO$_4$) and concentrated to yield 5-ethoxycarbonyloxy-2-nitrobenzoic acid (9.8 g) with a melting point of 126°–130°.

(c) Preparation of N-methanesulphonyl-5-hydroxy-2-nitrobenzamide.

The product from (b) (0.4 g) was heated and stirred under reflux with thionyl chloride (2 ml) for 90 minutes. The excess of thionyl chloride was removed under reduced pressure, acetonitrile added, and the solution re-evaporated. Methanesulphonamide (0.4 g), butyl acetate (8 ml) and caesium fluoride (2.4 g) were added and the mixture stirred and heated under reflux for 2 hours. The solvent was decanted from a dark tar. The tar was washed twice with hexane and then triturated with water and then agitated with 2-molar hydrochloric acid and ether. The ether layer was washed successively with water and brine and then dried and evaporated. The residue was purified by thin layer chromatography on silica gel using hexane: ethyl acetate: acetic acid (45:55:2) as the solvent. The major band was extracted with acetonitrile and methanol. The extract was filtered and evaporated. Hydrochloric acid (2 molar) was added and evaporated; the residue was dissolved in a mixture of ether and ethylacetate, and the solution filtered and evaporated. The residue was homogeneous when examined by thin layer chromatography and was identified as the required compound (m.p. 202°–206°) by its mass spectrum and nuclear magnetic resonance spectrum.

EXAMPLE 2

This Example illustrates the preparation of 2-nitro-5-(2-chloro-5-fluoro-4-trifluoromethylphenoxy) toluene by the process of claim 1. 3-Chloro-4,5-difluorobenzotrifluoride (1.62 g) and 3-methyl-4-nitrophenol (0.92 g) were stirred with anhydrous potassium carbonate (0.825 g) in dimethyl sulphoxide for 90 minutes and then left overnight. The mixture was then stirred at 60° for a further 8 hours, cooled, and poured into an excess of dilute hydrochloric acid. The mixture was extracted with ethyl acetate and the extract washed, dried and evaporated to give a brown oil. This was distilled (bath temperature 210° C., pressure 15 Torr) to give a yellow oil. This was taken up in ether and the ether solution washed repeatedly with dilute sodium hydroxide. The ether solution was then washed with water, dried, and evaporated to give a yellow oil, which crystallised on standing to give a pale yellow solid, with a melting point of 72°–73°. This was identified as the required product by its analysis, NMR, and IR spectrum.

EXAMPLE 3

This Example illustrates the preparation of 3-(2-chloro-6-fluoro-4-trifluoromethylphenoxy) benzoic acid by the process of claim 1. 3-Chloro-4,5-difluorobenzotrifluoride (0.54 g) and 3-hydroxybenzoic acid (0.28 g) were stirred with anhydrous potassium carbonate (0.55 g) in dimethyl sulphoxide (10 ml) for 2 hours at room temperature and then at 40° C. for 5 hours. The mixture was then left overnight at room temperature, and then heated at 75° for a further 12 hours. The mixture was then poured into dilute hydrochloric acid. The white precipitate was collected and dried to give the required product, with a melting point of 166°–167° C. Nitration of this product gave 5-(2-chloro-6-fluoro-4-trifluoromethylphenoxy)-2-nitrobenzoic acid.

EXAMPLE 4

This Example illustrates the preparation of 3-chloro-4,5-difluorobenzotrifluoride and 3,4,5-trifluorobenzotrifluoride.

(a) Preparation of 2,6-dichloro-4-trifluoromethylaniline

Chlorine was passed into a solution of p-trifluoromethylaniline (3.46 kg) in glacial acetic acid (7 liters). After 90 minutes the temperature had reached 60° and a solid was separating. Chlorination was continued for 13.5 hours, keeping the temperature between 60° and 90° with occasional warming. The suspension was filtered and the residue washed with 1 liter of cold acetic acid. The residue was then twice stirred with water (8 liters) and sucked dry on the filter to give the required dichloro compound.

(b) Preparation of 3,4,5-trichlorobenzotrifluoride 2,6-Dichloro-4-trifluoromethylaniline (3.3 kg) in concentrated hydrochloric acid (25 liters) was stirred for 1 hour and then cooled to $-6°$ C. A solution of sodium nitrite (1.41 kg) in water (3 liters) was added over a period of 4 hours keeping the temperature between $-5°$ and $-12°$. The mixture was then stirred between $-5°$ and 0° until all solid had dissolved (3.5 hours). The mixture was then added in 2 liter portions over a period of 35 minutes to a solution of cuprous chloride (1.5 kg) in concentrated hydrochloric acid with stirring. The dark solution was left to stand for 30 minutes, filtered, and extracted with dichloromethane ($1 \times 15$ liters, then $2 \times 10$ liters). The extracts were washed with water ($2 \times 25$ liters) dried ($MgSO_4$) and evaporated under reduced pressure to give 3,4,5-trichlorobenzotrifluoride (2.2 kg) with a boiling range of 98°–100°/40 Torr.

(c) Preparation of 3-chloro-4,5-difluorobenzotrifluoride and 3,4,5-trifluorobenzotrifluoride.

The above trichloro compound (750 g) was added to a solution of potassium fluoride (900 g) in sulpholane (3.75 liters) which had previously been heated until liquid was distilling from the mixture at a still-head temperature of 270°, so as to dry the reactants. The flask was then fitted with a Vigreaux column (24" long) (61 cm) and a reflux divider. The mixture was heated under reflux for 5 hours, and the reflux divider then adjusted to collect liquid boiling at 120° or less. Heating was continued for 25 hours and 530 grams of distillate was collected. This was combined with a further quantity (520 g) of liquid obtained from a similar preparation. A portion (745 g) was distilled at atmospheric pressure after washing with water and drying (Mg SO$_4$). The first runnings of the distillate (b.p. 98°–106°) were pure 3,4,5-trifluorobenzotrifluoride (15 g). The next fraction (b.p. 106°–130°) contained a mixture of the trifluoro compound with some 3-chloro-4,5-difluorobenzotrifluoride (55 g). Finally, essentially pure 3-chloro-4,5-difluorobenzotrifluoride (b.p. 130°–136°) was collected (580 g). A part of this material was re-heated with potassium fluoride in sulpholane under reflux for 36 hours. Fractional distillation through a Vigreaux column as described above then gave a further quantity of 3,4,5-trifluorobenzotrifluoride and some unchanged 3-chloro-4,5-difluorobenzotrifluoride.

The 3,4,5-trichlorobenzotrifluoride required for use in the above synthesis may also be prepared by an alternative route described below:

(a) Preparation of 4-chloro-3,5-diaminobenzotrifluoride by iron reduction of 4-chloro-3,5-dinitrobenzotrifluoride 4-Chloro-3,5-dinitrobenzotrifluoride (43 kg), isopropanol (150 liters), and iron powder (43 kg) were heated under reflux. Hydrochloric acid (36% w/v; 4.77 liters) in water (56 liters) was then added over a period of 3 hours 40 minutes. Heating was discontinued during the addition, since the reaction was sufficiently exothermic to maintain reflux. After addition was complete, the mixture was heated under reflux for another 2 hours 15 minutes. The isopropanol and water was then distilled off over a period of 4 hours. Dichloromethane (100 liters) was then added and the mixture stirred with Hyflo Supercel (Hyflo Supercel is a Trade Mark for a filtration aid comprising diatomaceous earth), and filtered. The residue was thoroughly washed with dichloromethane. The dichloromethane was evaporated to give an oil which was poured on to trays to solidify. The yield was 28 kg (84% of the theoretical yield based on the dinitro starting material) of 4-chloro-3,5-diaminobenzotrifluoride with a melting point of 79°–85° C.

Alternative preparation of 4-chloro-3,5-diaminobenzotrifluoride by catalytic hydrogenation of 4-chloro-3,5-dinitrobenzotrifluoride 4-Chloro-3,5-dinitrobenzotrifluoride (5.4 g) in ethanol (50 ml) was heated to 50° and stirred with 5% platinum on carbon catalyst (0.1 g) under an atmosphere of hydrogen in a pressure vessel (hydrogen pressure 30 pounds per square inch). After 8 hours the catalyst was filtered off and the solvent removed to give the required diamino compound as a buff solid with a melting point of 83°–85° (literature value 88°–91°).

(b) Preparation of 3,4,5-trichlorobenzotrifluoride from 4-chloro-3,5-diaminobenzotrifluoride Concentrated hydrochloric acid (75 liters) was cooled to $-20°$ C. and stirred while a solution of sodium nitrite (10.5 kg) in water (22.5 liters) and a solution of 4-chloro-3,5-diaminobenzotrifluoride (7.5 kg) in dichloromethane (22.5 liters) were both slowly added. The total time taken for addition was 6 hours. The temperature of the mixture was kept between $-12°$ and $-6°$. The mixture was stirred for a further 30 minutes at between $-6°$ and $-9°$, and then transferred slowly on to a mixture of cuprous chloride (7 kg) and concentrated hydrochloric acid (40 liters), kept at a temperature between 13° and 23° by water-cooling. The mixture was then stirred for about 90 minutes at 15°. The dichloromethane layer was separated and the aqueous layer re-extracted with more dichloromethane ($2 \times 20$ liters). The combined dichloromethane extracts were washed with water ($3 \times 30$ liters) and then evaporated leaving an oil (6.06 kg). This was distilled (some material lost by spillage) at a pressure of 30 Torr to give the required 3,4,5-trichlorobenzotrifluoride (boiling range 84°–92°). The yield (based on 4-chloro-3,5-diaminobenzotrifluoride starting material) was 36% of the theoretical.

EXAMPLE 5

This Example illustrates the preparation of 2-chloro-5-(2-chloro-6-fluoro-4-trifluoromethylphenoxy)-benzoic acid by the process of claim 1.

2-Chloro-5-hydroxybenzoic acid (1.5 g), 3-chloro-4,5-difluorobenzotrifluoride (1.88 g) and potassium carbonate (5 g) were heated with stirring in dimethylsulphoxide at 80° for 2.5 hours. The mixture was agitated with ethyl acetate and dilute hydrochloric acid. The ethyl acetate layer was separated, washed with water, dried ($MgSO_4$) and evaporated to give a clear oil. Trituration with petroleum ether (b.p. 60°–80°) gave a solid (2.57 g) having a melting point of 134° C., identified as the required compound.

The compound was converted to the acid chloride by heating under reflux with excess of thionyl chloride for 3 hours. By reaction of this acid chloride with methanesulphonamide, ethanesulphonamdie, and isopropanesulphonamide in the presence of a base (e.g. pyridine) as described in published European patent application No. 3416 (the disclosure of which is herein incorporated by reference) the following sulphonamides were prepared. (The symbol Ar in the formulae below stands for the group:

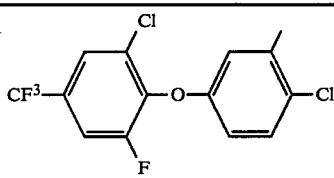

| Sulphonamide Compound | Melting point °C. |
|---|---|
| $ArCONHSO_2CH_3$ | 171–173 |
| $ArCONHSO_2C_2H_5$ | 172–174 |
| $ArCONHSO_2C_3H_7iso$ | 128–130 |

Similarly, the following esters could be prepared by reaction of the acid chloride with methanol, ethanol, or n-propanol:
$Ar\ CO_2\ CH_3$
$Ar\ CO_2\ C_2H_5$
$Ar\ CO_2\ C_3H_7$

EXAMPLE 6

This Example illustrates the preparation of 3-(2,6-difluoro-4-trifluoromethylphenoxy)benzoic acid by the process of claim 1.

A solution of 3-hydroxybenzoic acid (5.5 g) and 3,4,5-trifluorobenzotrifluoride (8.3 g) in dimethylformamide (50 ml) was stirred with anhydrous potassium carbonate (14 g) for 4 hours at 100°. The mixture was then diluted with water (200 ml) and acidified. The mixture was extracted with ether and the ether extract dried and evaporated to give the required compound (7.2 g) with a melting point of 140°–146°. Nitration of this product gave 2-nitro-5(2,6-difluoro-4-trifluoromethyl)benzoic acid.

EXAMPLE 7

This Example illustrates the preparation of 5-(2-chloro-6-fluoro-4-trifluoromethylphenoxy)-2-nitrobenzoic acid by the process of claim 1.

5-Ethoxycarbonyloxy-2-nitrobenzoic acid (6.12 g) was dissolved in a solution of potassium hydroxide (3.2 g of 85% pure material) in water (10 ml) and heated under reflux for 2 hours, to cleave off the ethoxy-carbonyl residue and form the di-potassium salt of 3-carboxy-4-nitrophenol. The solution so prepared was mixed with toluene and distilled until the water had been removed. Dimethyl sulphoxide (50 ml) was added and the mixture distilled until the vapour temperature reached 190°. A further quantity (50 ml) of dimethyl sulphoxide (50 ml) was then added, together with 3-chloro-4,5-difluorobenzotrifluoride (5.43 g), and the mixture heated at 100° for 4 hours. The mixture was diluted with water (200 ml) and acidified with dilute hydrochloric acid. The mixture was extracted twice with ether and the extracts washed with water, dried and evaporated. The brown oil remaining was crystallised from carbon tetrachloride to give the required compound (2 g) with a melting point of 145°–148°.

The 3-ethoxycarbonyloxybenzoic acid required as starting material was prepared by treating a cooled solution of 3-hydroxybenzoic acid in 2 molar proportions of aqueous sodium hydroxide with ethyl chloroformate and then isolating the product by acidifying the reaction mixture and extracting with chloroform. The 3-ethoxycarbonyloxybenzoic acid had a melting point of 70°–72°.

The 5-(2-chloro-6-fluoro-4-trifluoromethylphenoxy)-2-nitrobenzoic acid prepared as above was converted to its corresponding acid chloride by heating under reflux in excess of thionyl chloride for 3 hours. The excess of thionyl chloride was removed and the acid chloride was reacted with the appropriate alkanesulphonamide in the presence of pyridine as described in published European Patent Application 3416 to obtain the sulphonamides listed in Table 1 below. In this table, the symbol Ar stands for the 5-(2-chloro-6-fluoro-4-trifluoromethylphenoxy)-2-nitrophenyl group.

TABLE 1

| Sulphonamide | Melting point °C. |
|---|---|
| $ArCONHSO_2CH_3$ | 172–173 |
| $ArCONHSO_2C_2H_5$ | 160–161 |
| $ArCONHSO_2C_3H_7iso$ | 155–156 |
| $ArCONHSO_2C_3H_7n$ | 153–154 |
| $ArCONHSO_2C_4H_9n$ | 186–187 |

Reaction of the acid chloride with alcohols gave esters (see Table 2 below, in which the symbol Ar has the same meaning as in Table 1)

TABLE 2

| |
|---|
| $ArCO_2CH_3$ |
| $ArCO_2C_2H_5$ |
| $ArCO_2C_3H_7n$ |
| $ArCO_2C_4H_9n$ |
| $ArCO_2C_4H_9iso$ |

Similarly 5-(2,6-difluoro-4-trifluoromethylphenoxy)-2-nitrobenzoic acid, prepared according to Example 6 was converted to the corresponding acid chloride, which was then in turn converted to the N-alkanesulphonyl amides listed in Table 3. In this Table, the symbol Ar stands for the 5-(2,6-difluoro-4-trifluoromethylphenoxy)-2-nitrophenyl radical.

TABLE 3

| Sulphonamide | Melting point °C. |
|---|---|
| $ArCONHSO_2CH_3$ | 204–205 |
| $ArCONHSO_2C_3H_7n$ | 148–149 |

The acid chloride was also used to prepare the esters listed in Table 4 below; in this Table, the symbol Ar has the same meaning as in Table 3.

TABLE 4

| |
|---|
| $ArCO_2CH_3$ |
| $ArCO_2C_2H_5$ |
| $ArCO_2C_3H_7n$ |
| $ArCO_2C_4H_9n$ |

We claim:
1. A process of preparing compounds of the formula (II)

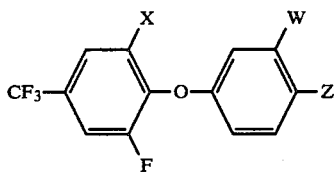

(II)

wherein X is fluorine, chlorine or bromine, Z is hydrogen, fluorine, chlorine, bromine, iodine, nitro, or cyano, and W is a methyl group, a cyano group, an acetyl group, or a group

wherein R is OH; OM wherein M is a cation; $OR^1$ wherein $R^1$ is an optionally substituted aliphatic radical; $-NR^2R^3$ wherein $R^2$ and $R^3$ are each hydrogen or an optionally substituted aliphatic radical; or $-NHSO_2R^4$ wherein $R^4$ is an alkyl radical of 1 to 6 carbon atoms, which comprises reacting a 3-X-substituted-4,5-difluorobenzotrifluoride with a salt of a 3,4-W,Z-substituted phenol in a solvent or diluent for the reactants, and in the case when W is $-CO_2H$ or $-CONHSO_2R^4$ acidifying the product of the reaction, and recovering the compound of formula (II).

2. A process as claimed in claim 1 wherein X is chlorine or fluorine, W is a $-CO_2H$ or $-CONHSO_2R^4$ group and Z is chlorine or a nitro group.

3. A benzotrifluoride compound of the formula

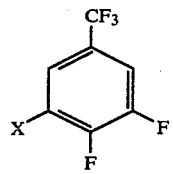

wherein X is fluorine, chlorine or bromine.

4. A process of preparing a 3-halogeno-4,5-difluorobenzotrifluoride of the formula defined in claim 3 which comprises reacting a 3,4,5-trihalogenobenzotrifluoride of the formula

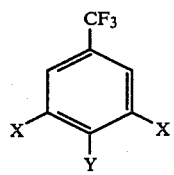

wherein X is fluorine, chlorine or bromine and Y is fluorine or chlorine provided that X and Y are not both fluorine with an alkali metal fluoride at a temperature of at least 130° C. and separating the desired 3-halogeno-4,5-difluorobenzotrifluoride by distillation.

5. A process as claimed in claim 4 wherein 3-chloro-4,5-difluorobenzotrifluoride is prepared by reaction of 3,4,5-trichlorobenzotrifluoride with an alkali metal fluoride.

6. A process as claimed in claim 4 wherein 3,4,5-trifluorobenzotrifluoride is prepared by reaction of 3,4,5-trichlorobenzotrifluoride with an alkali metal fluoride.

7. A process of preparing 3,4,5-trifluorobenzotrifluoride which comprises reacting 3-chloro or 3-bromo-4,5-difluorobenzotrifluoride with an alkali metal fluoride at a temperature of at least 130° and separating the 3,4,5-trifluorobenzotrifluoride by distillation.

* * * * *